United States Patent [19]

Levin et al.

[11] Patent Number: 5,284,852

[45] Date of Patent: Feb. 8, 1994

[54] ANGIOTENSIN II RECEPTOR BLOCKING 2,3,6-SUBSTITUTED QUINAZOLINONES

[75] Inventors: Jeremy I. Levin, Nanuet; Aranapakam M. Venkatesan, Elmhurst, both of N.Y.

[73] Assignee: American Cyanamid Company, Wayne, N.J.

[21] Appl. No.: 52,941

[22] Filed: Apr. 23, 1993

[51] Int. Cl.$^5$ .................. A61K 31/505; C07D 239/91; C07D 403/10; C07D 401/14
[52] U.S. Cl. ..................... 514/259; 544/90; 544/229; 544/284; 544/287
[58] Field of Search ............... 544/284, 287, 289, 290; 514/259

[56]  References Cited

U.S. PATENT DOCUMENTS

| | | | |
|---|---|---|---|
| 5,202,322 | 4/1993 | Allen | 514/228.2 |
| 5,204,354 | 4/1993 | Chakravarty et al. | 544/283 |
| 5,238,942 | 8/1993 | Chakravarty et al. | 544/284 |
| 5,240,928 | 8/1993 | Allen et al. | 544/284 |
| 5,252,574 | 10/1993 | Allen et al. | 544/287 |

FOREIGN PATENT DOCUMENTS

| | | | |
|---|---|---|---|
| 407342 | 1/1991 | European Pat. Off. | |
| 411766 | 2/1991 | European Pat. Off. | 544/284 |
| 445811 | 9/1991 | European Pat. Off. | |
| 481448 | 4/1992 | European Pat. Off. | |
| 512870 | 11/1992 | European Pat. Off. | |

*Primary Examiner*—Emily Bernhardt
*Attorney, Agent, or Firm*—T. S. Szatkowski

[57]  ABSTRACT

This disclosure describes novel 2,3,6-substituted quinazolinones having the formula:

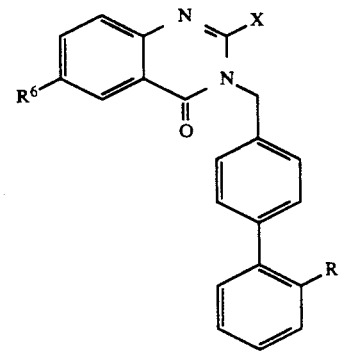

wherein $R^6$, X and R are as described in the specification which have activity as angiotensin II (AII) antagonists.

25 Claims, No Drawings

ANGIOTENSIN II RECEPTOR BLOCKING 2,3,6-SUBSTITUTED QUINAZOLINONES

BACKGROUND OF THE INVENTION

1. Field of the Invention

This invention relates to certain novel 2,3,6 substituted quinazolinone compounds which have demonstrated activity as angiotensin II (AII) antagonists and are therefore useful in alleviating angiotensin induced hypertension and for treating congestive heart failure.

SUMMARY OF THE INVENTION

According to the present invention, there are provided novel compounds of Formula I which have angiotensin II-antagonizing properties and are useful as antihypertensives:

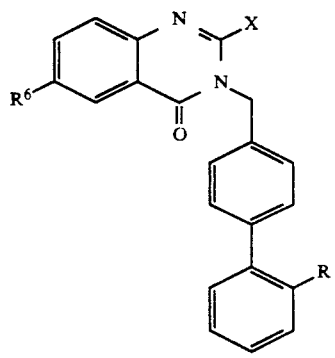

Formula I wherein:
R is

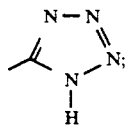

X is straight or branched chain lower alkyl of 3 to 5 carbon atoms;
n is 0 to 3;
$R^6$ is

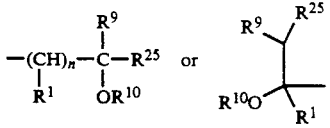

where $R^1$, $R^9$ and $R^{25}$ can be the same or different;
$R^1$ is H, straight or branched chain lower alkyl of 1 to 4 carbon atoms, phenyl, substituted phenyl (substitution selected from mono-lower alkyl of 1 to 4 carbon atoms, —$CF_3$, —$NH_2$, nitro, O-alkyl of 1 to 4 carbon atoms, F, Cl, Br), pyridine, thiophene or furan;
$R^9$ is H, straight or branched chain lower alkyl of 1 to 4 carbon atoms, phenyl, substituted phenyl (substitution selected from mono-lower alkyl of 1 to 4 carbon atoms, —$CF_3$, —$NH_2$, nitro, O-alkyl of 1 to 4 carbon atoms, F, Cl, Br), pyridine, thiophene or furan;
$R^{10}$ is phenyl, substituted phenyl (substitution selected from mono-lower alkyl of 1 to 4 carbon atoms, —$CF_3$, —$NH_2$, F, Cl, Br, nitro, or O-alkyl of 1 to 4 carbon atoms);
$R^{25}$ is H, straight or branched chain lower alkyl of 1 to 4 carbon atoms, phenyl, substituted phenyl (substitution selected from mono-lower alkyl of 1 to 4 carbon atoms, —$CF_3$, —$NH_2$, nitro, O-alkyl of 1 to 4 carbon atoms, F, Cl, Br), pyridine, thiophene or furan; and the pharmaceutically acceptable salts thereof.

The present invention also provides novel intermediate compounds, methods for making the novel 2,3,6 substituted quinazoline angiotensin II antagonizing compounds, methods of using the novel quinazolinone angiotensin II antagonizing compounds to treat hypertension, congestive heart failure and to antagonize the effects of angiotensin II.

DETAILED DESCRIPTION OF THE INVENTION

The novel compounds of the present invention are prepared according to the following reaction schemes.

Referring to Scheme I, the corresponding anthranilic acid 2, where $R^{20}$ is I, Br or $CH_3$, are heated to reflux in alkyl acid anhydride 3 wherein X is straight or branched chain lower alkyl of 3 to 5 carbon atoms to provide the 4H-3,1-benzoxazin-4-ones 4 which are isolated by concentrating the reaction mixtures and used without further purification. When the 4H-3,1-benzoxazin-4-ones 4 are refluxed in ethyl alcohol containing ammonia, or ammonium hydroxide solution, the quinazolinone intermediates 5 are obtained.

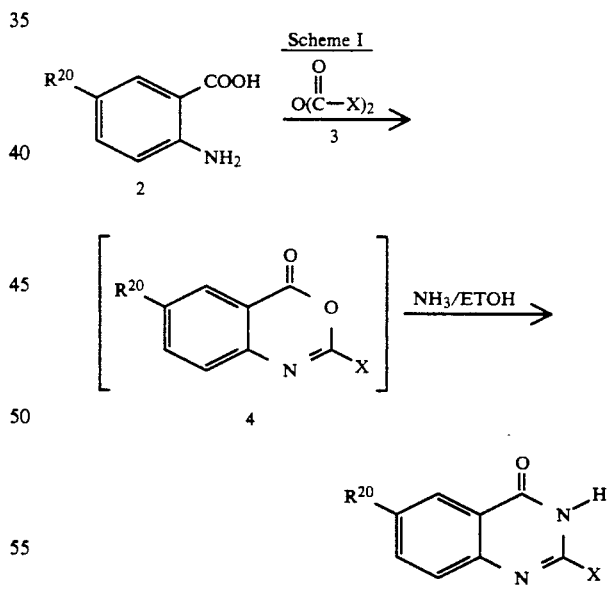

The quinazolinone intermediates 5 are modified according to the following reaction schemes to obtain the novel quinazolinone Angiotensin II antagonist compounds of the present invention.

In Scheme II, 6-methylquinazoline 6, as prepared by Scheme I, is brominated with N-bromosuccinimide to give the bromomethyl compound 7. Hydrolysis of the bromide with aqueous potassium carbonate in dimethylsulfoxide yields the primary alcohol 8. The alcohol 8 is oxidized with pyridinium dichromate in N,N-dimethylformamide to afford aldehyde 9. The aldehyde 9 is reacted with a variety of Grignard Reagents $R^9MgBr$ or lithium reagents $R^9Li$ in tetrahydrofuran where $R^9$ is hereinbefore defined with the proviso that for this reaction scheme $R^9$ is not H to give the desired secondary alcohol 10. Alcohol 10 is oxidized with pyridinium dichromate in N,N-dimethylformamide to afford ketone 11. Alternatively, aldehyde 9 is reacted with a variety of Grignard Reagents $R^1MgBr$ or lithium reagents $R^1Li$ in tetrahydrofuran where $R^1$ is hereinbefore defined with the proviso that for this reaction scheme $R^1$ is not H to give the desired secondary alcohol 10a. Alcohol 10a is oxidized with pyridinium dichromate in N,N-dimethylformamide to afford keytone 11a. Reduction of aldehyde 9 with sodium borohydride gives primary alcohol 8. The ketone 11 is reacted with a variety of Grignard Reagents $R^{25}MgBr$ or lithium reagents $R^{25}Li$ in tetrahydrofuran where $R^{25}$ is hereinbefore defined with the proviso that for this reaction scheme $R^{25}$ is not H to give the desired alcohol 12.

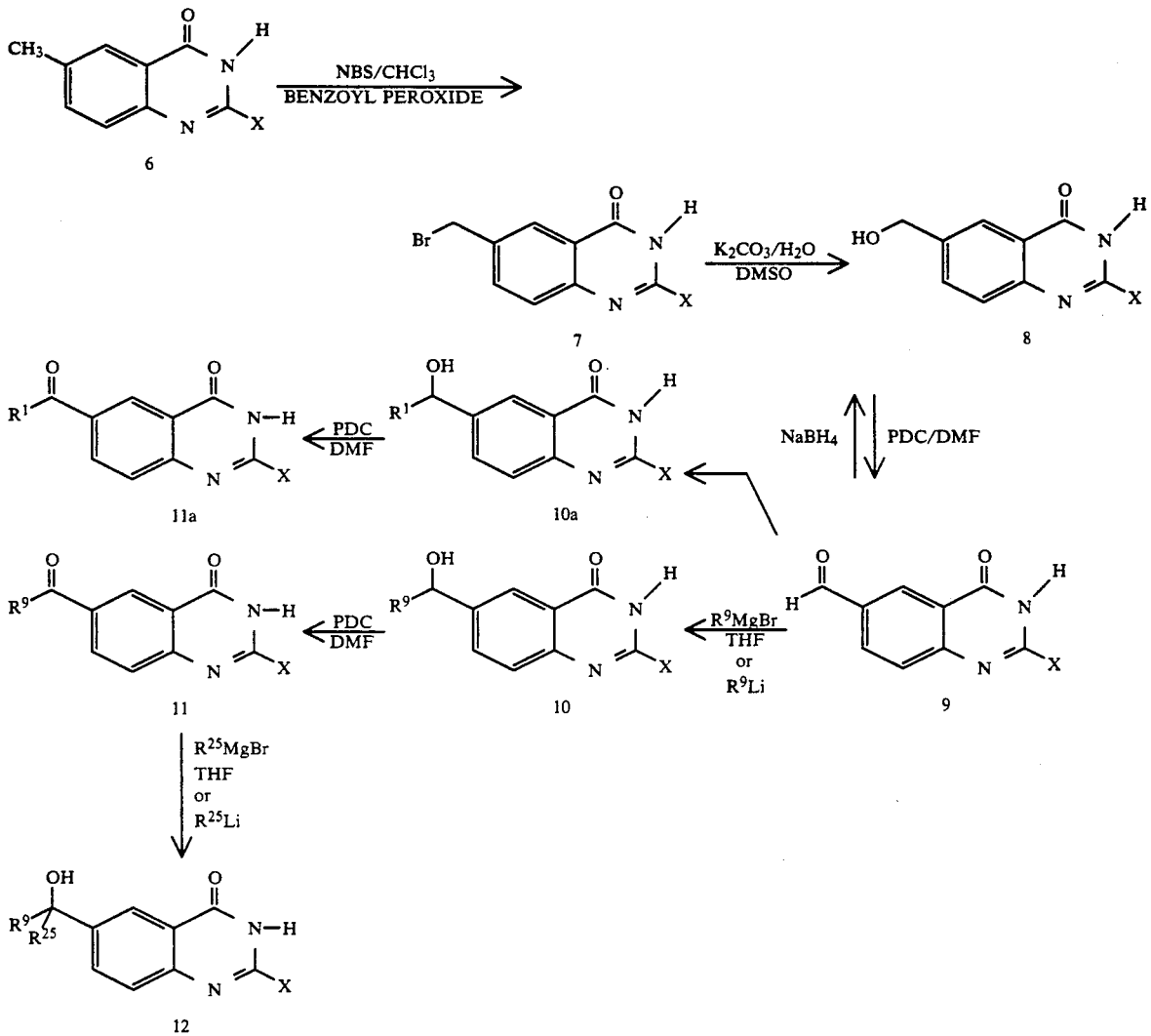

Scheme II

As shown in Scheme III, 2-alkylsubstituted-6-iodo-4(1H)-quinazolinone 13, prepared by Scheme I is reacted via a palladium catalyzed formylation to give 9 via an alternative route. Additionally, 13 is converted to ester 14 by palladium (II) catalyzed coupling in the presence of carbon monoxide and methanol. Reduction of 14 with lithium aluminum hydride in tetrahydrofuran gives alcohol 8. Alcohol 8 is oxidized with pyridinium dichromate to yield aldehyde 9 via another alternative route. The ester 14 is reacted with a variety of Grignard Reagents $R^9MgBr$ or lithium reagents $R^9Li$ in tetrahydrofuran where $R^9$ is hereinbefore defined with the proviso that for this scheme $R^9$ is not H to give alcohol 15.

Scheme III

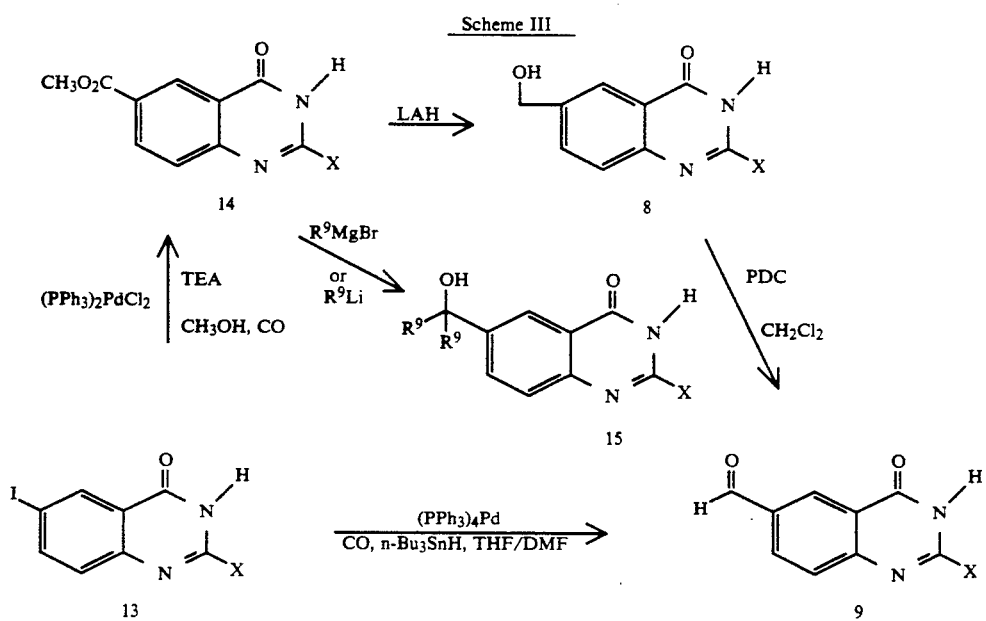

As shown in Scheme IV, the palladium (II) catalyzed coupling of (trimethylsilyl)acetylene with 2-alkylsubstituted-6-iodo-4(1H)-quinazolinone 13 yields the acetylenic quinazolinone 16. Desilylation of the acetylene with sodium hydroxide in water-methanol gives the terminal acetylene 17. Hydration of acetylene 17 with catalytic mercuric sulfate-sulfuric acid in acetic acid affords methyl ketone 18. Reduction of ketone 18 with sodium borohydride gives alcohol 23. The palladium (II) catalyzed coupling of substituted acetylenes where $R^{25}$ is as defined hereinbefore with 2-alkylsubstituted-6-iodo-4(1H)-quinazolinone 13 yields the acetylenic quinazolinone 19. Hydration of 19 with catalytic mercuric sulfate-sulfuric acid in acetic acid gives a mixture of ketones 20 and 21. The ketones are separated by chromatography. Reduction of ketone 20 with sodium borohydride in ethanol gives secondary alcohol 22. Reduction of ketone 21 with sodium borohydride gives alcohol 24.

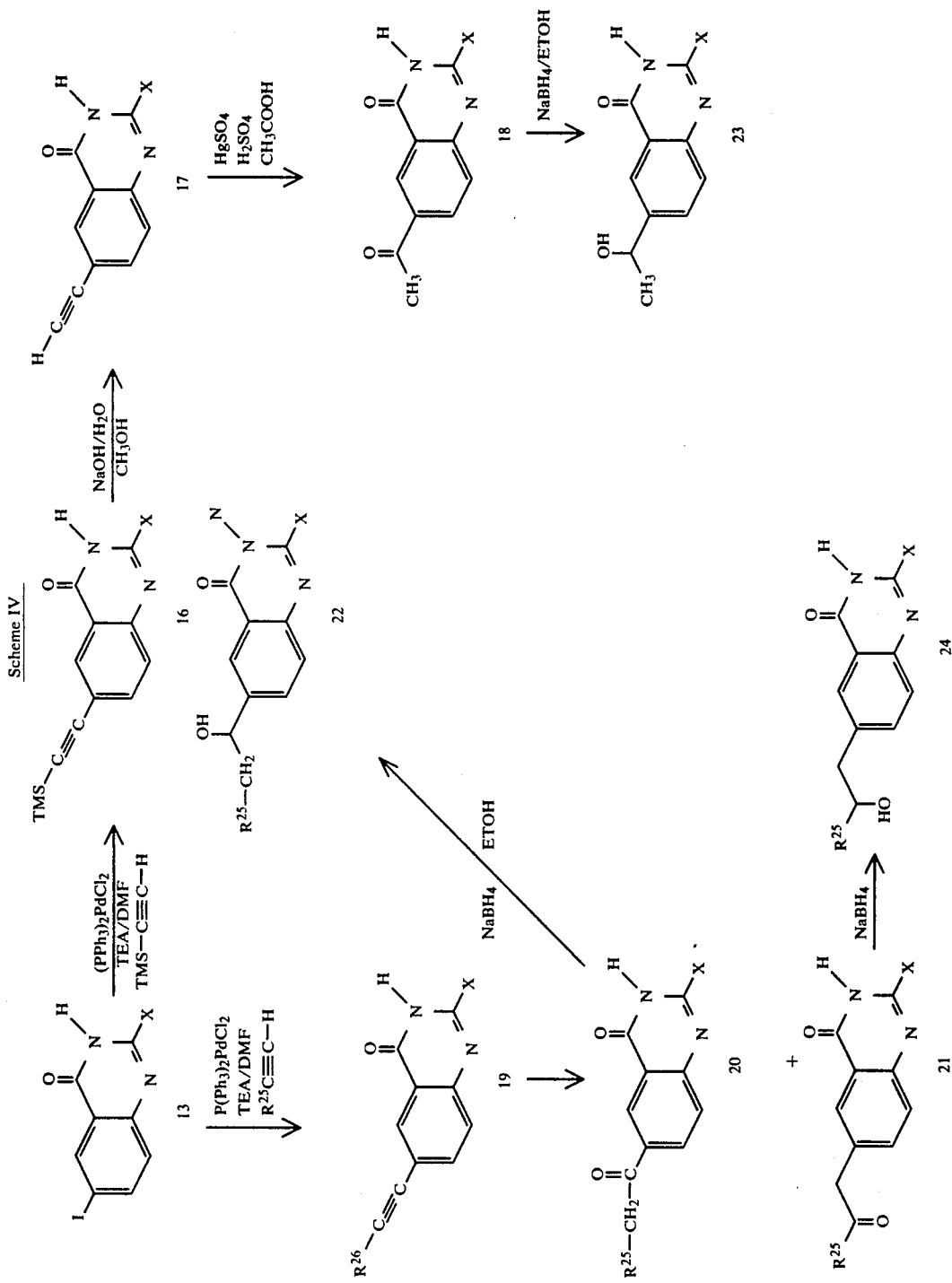

In addition as shown in Scheme V, acetylene 17 is hydrogenated over 5% palladium-barium sulfate in pyridine to give either the terminal olefin 25 or the ethyl substituted quinazolinone 26. Also, acetylene 19 is hydrogenated over 5% palladium-barium sulfate in pyridine to give olefin 27 and alkyl substituted quinazolinone 28. Olefin 27 with the proviso that $R^{25}$ for this scheme is hydrogen is reacted with borane followed by hydrogen peroxide, to afford alcohol 29. Additionally, 13, is converted to 25 by reaction with vinyltin in the presence of tetrakis(triphenylphosphine)palladium.

As shown in Scheme VI, olefinated quinazolinones 32 are obtained through Wittig olefination or Wadsworth-Emmons olefination of the aldehyde or ketone 11a, wherein $R^1$ is hereinbefore defined by reaction with 30 or 31 in the presence of base wherein $R^9$ and $R^{25}$ are as hereinbefore defined and with the further addition of $-CO_2R^{19}$ where $R^{19}$ is lower alkyl of 1 to 4 carbon atoms. Reduction of 32 with hydrogen affords 33. In the case where $R^9$ is $-CO_2R^{19}$, when 33 is reduced with lithium aluminum hydride, alcohol 34 results. Reaction of olefin 32 with borane and hydrogen peroxide affords a mixture of alcohols 35 and 36 which can be separated by chromatography.

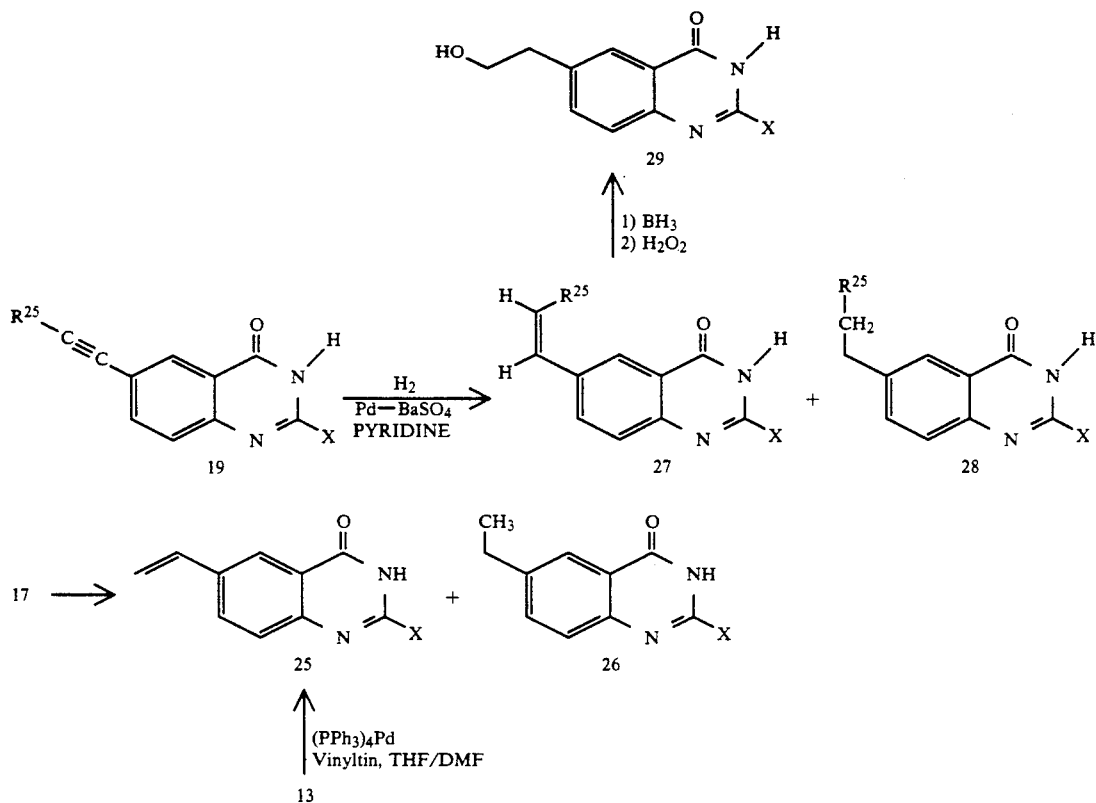

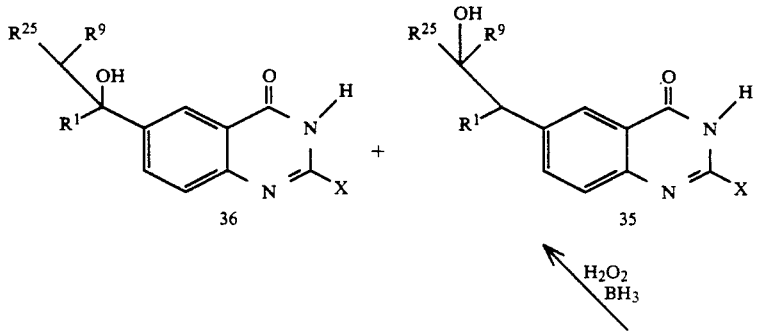

Scheme VI

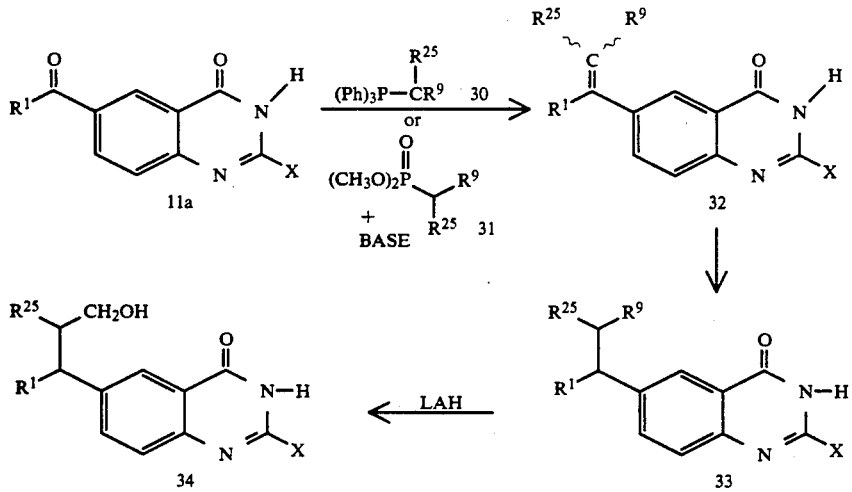

Scheme VII

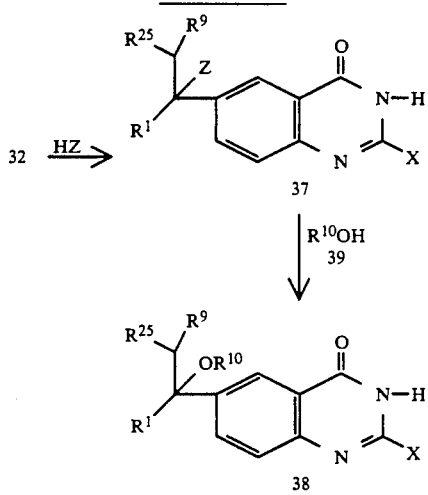

As shown in Scheme VII, olefinated quinazolinones 32 are reacted with HZ were Z is Cl or Br to afford halide 37. Tertiary alcohols 12 on 15 are also reacted with HZ to afford the corresponding halide. Halides 37 are converted to 38 by reaction with phenols 39 where $R^{10}$ is hereinbefore defined, by the method of (H. Masada and Y. Oishi, Chemistry Letters, 57–58 (1978)) or (F. Camps, J. Coll, and J. M. Moreto, Synthesis, 186–188 (1982)).

As described in EP 0 497 150, biphenyl 41 is attached to quinazolinone intermediate 35 by initially alkylating the quinazolinone with a para-substituted benzyl bromide and subsequently attaching a second phenyl moiety containing a trityl protected tetrazole or a cyano via a transition metal catalyzed coupling at the para position of the first phenyl ring. Alternatively, the coupling of quinazolinone intermediate 35, wherein $R^1$, $R^9$, $R^{25}$ and X are hereinbefore defined, with biphenyl 41 where $R^{30}$ is a trityl protected tetrazole prepared by the methods of N. B. Mantlo, J. Med. Chem. 34, 2922–2925 (1991) or cyano prepared by the methods outlined in D. J. Carini, J. Med. Chem. 34, 2525–2547 (1991) is illustrated in Scheme VIII and gives coupled product 42 by dissolving 35, and 41 in acetone or another suitable solvent such as N,N-dimethylformamide, N,N-dimethylacetamide, N-methylpyrrolidinone, methanol, ethanol, t-butanol, tetrahydrofuran, dioxane or dimethylsulfoxide, in the presence of excess potassium carbonate or another suitable base such as sodium carbonate, cesium carbonate, sodium ethoxide, lithium methoxide, lithium diisopropylamide, lithium bis(trimethylsilyl)amide, sodium t-butoxide or potassium t-butoxide for 2–48 hours, at 20°–60° C. The obtained alkylated quinazolinones 42 may be purified by chromatography or used as is in further transformations and/or deprotection. Biphenyl 41 may similarly be attached to quinazolinone intermediates 8, 10, 12, 15, 22, 23, 24, 29, 34, 36 and 38.

Deprotection of the trityl group is accomplished by refluxing an aqueous acetone solution of the alkylated quinazolinone 42 with a catalytic amount of hydrochloric acid or other suitable acid such as sulfuric, trifluoroacetic or hydrogen chloride for 2–24 hours. Additionally, heating 42 in tetrahydrofuran-methanol removes the trityl protecting group and affords 43. Reaction of 42 where $R^{30}$ is cyano with sodium azide in the presence of tri-n-butyltin chloride in refluxing xylene affords the desired tetrazole 43. Contemplated equivalents to tri-n-butyltin chloride include tri-(lower alkyl $C_1$–$C_4$) tin chlorides and bromides. Contemplated equivalents to sodium azide include potassium azide, and lithium azide.

Scheme VIII

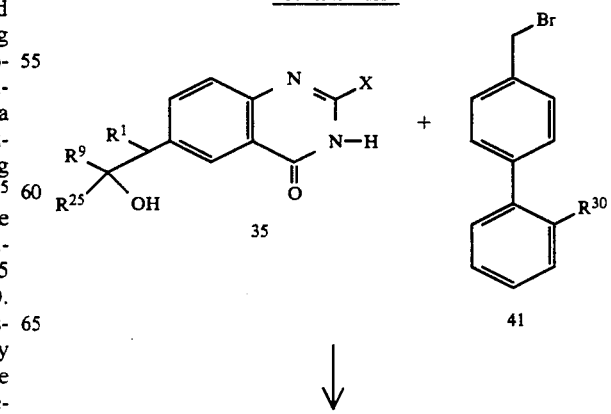

-continued
Scheme VIII

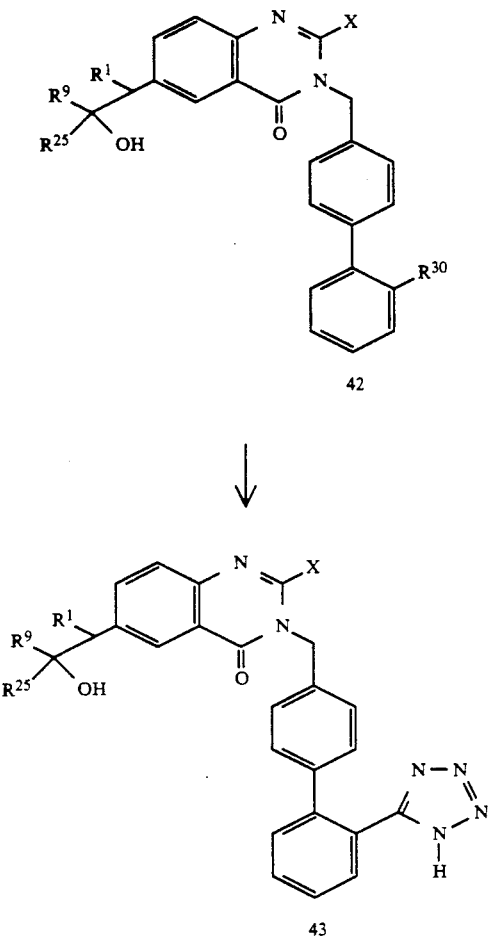

Scheme IX

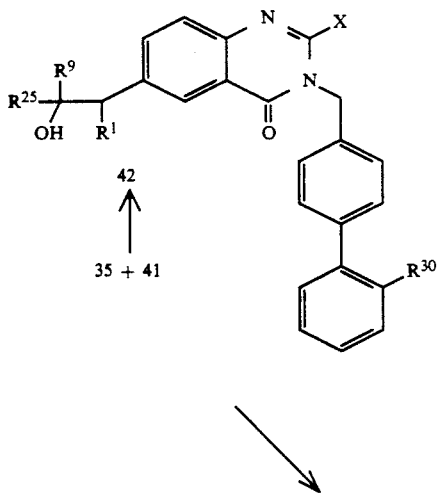

-continued
Scheme IX

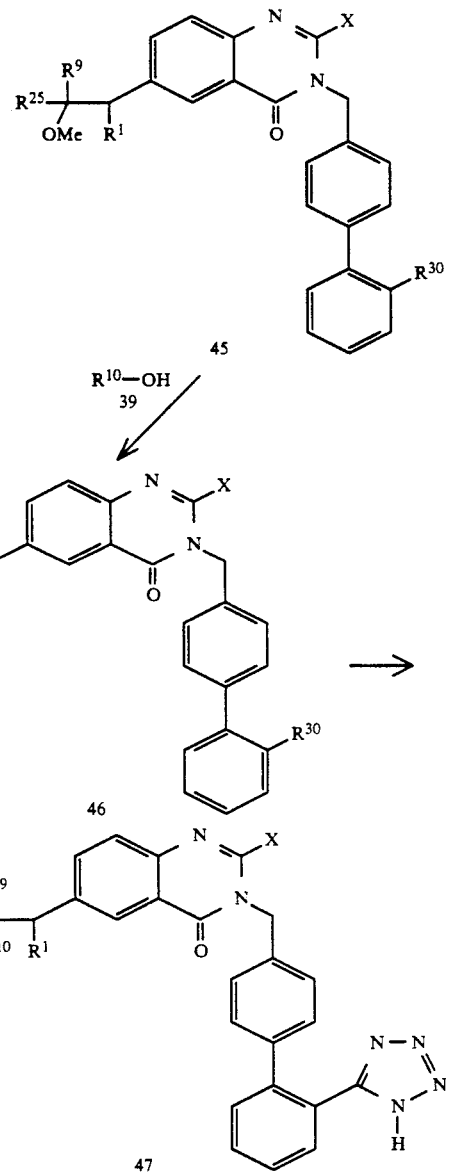

As shown in scheme IX, alcohol 42 wherein $R^1$, $R^9$, $R^{25}$, $R^{30}$ and X are hereinbefore defined is reacted with methanesulfonyl chloride in the presence of triethylamine in tetrahydrofuran at $-78°$ C. to room temperature to afford mesylate 45. The mesylate 45 and a phenol $R^{10}OH$, 39, wherein $R^{19}$ is hereinbefore defined are dissolved in acetone or other suitable solvent such as N,N-dimethylformamide, N,N-dimethylacetamide, N-methylpyrrolidinone, tetrahydrofuran, dioxane or dimethylsulfoxide, in the presence of potassium carbonate or another suitable base such as sodium carbonate, cesium carbonate, sodium hydride, potassium hydride, sodium methoxide, sodium ethoxide, lithium ethoxide, sodium t-butoxide or potassium t-butoxide for 2-48 hours, at 20°-60° C. to afford 46. Hydrolysis of 46 where $R^{30}$ is a trityl protected tetrazole with a catalytic amount of hydrochloric acid or other suitable acid such as sulfuric, trifluoroacetic or hydrogen chloride for 1-24 hours at room temperature or MeOH/THF at reflux affords the free tetrazole 47. Reaction of 46 where $R^{30}$ is cyano with sodium azide in the presence of tri-n-butyltin chloride in refluxing xylene affords the desired tetrazole 47. Alcohol substituted alkylated quinazolinones prepared from 8, 10, 12, 15, 22, 23, 24, 29, 34, 36 and 38 according to Scheme VIII may be similarly reacted.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. This will frequently necessitate judgement as to the order of synthetic steps, protecting groups, if required, and deprotection conditions. Substituents on the starting materials may be incompatible with some of the reaction conditions. Such restrictions to the substituents which are compatible with the reaction conditions will be apparent to one skilled in the art.

Pharmaceutically suitable salts include both the metallic (inorganic) salts and organic salts; a list of which is given in *Remington's Pharmaceutical Sciences*, 17th Edition, pg, 1418 (1985). It is well known to one skilled in the art that an appropriate salt form is chosen based on physical and chemical stability, flowability, hygroscopicity and solubility. Preferred salts of this invention for the reasons cited above include potassium, sodium, calcium, magnesium and ammonium salts.

Some of the compounds of the hereinbefore described schemes have centers of asymmetry. The compounds may, therefore, exist in at least two and often more stereoisomeric forms. The present invention encompasses all stereoisomers of the compounds whether free from other stereoisomers or admixed with other stereoisomers in any proportion and thus includes, for instance, racemic mixture of enantiomers as well as the diastereomeric mixture of isomers. The absolute configuration of any compound may be determined by conventional X-ray cyrstallography.

While the invention has been illustrated using the trityl protecting group on the tetrazole, it will be apparent to those skilled in the art that other nitrogen protecting groups may be utilized. Contemplated equivalent protecting groups include, benzyl, p-nitrobenzyl, propionitrile or any other protecting group suitable for protecting the tetrazole nitrogen. Additionally, it will be apparent to those skilled in the art that removal of the various nitrogen protecting groups, other than trityl, may require methods other than dilute acid.

The compounds of this invention and their preparation are illustrated by the following non-limiting examples.

EXAMPLE 1

2-Butyl-6-(methyl)-4(1H)-quinazolinone

Method A

To 20.0 g of 2-amino-5-methylbenzoic acid is added 60 ml of valeric anhydride. The mixture is heated at reflux for 18 hours and then concentrated under reduced pressure. The resulting brown solid residue is dissolved in a mixture of 200 ml of 30% of ammonium hydroxide solution and 300 ml of ethyl alcohol. This mixture is heated at reflux for 5 hours and then allowed to cool to room temperature. After cooling, the precipitate is collected by filtration. The cake is washed with ethanol and water, then dried under vacuum to give 8.92 g of the quinazolinone as a white solid. CI MASS SPEC MH+ =217.

EXAMPLE 2

2-Butyl-6-iodo-4(1H)-quinazolinone

The method of Example 1 is used with 2-amino-5-iodobenzoic acid to prepare the desired product, m.p. 257°–258° C.

EXAMPLE 3

2-Butyl-6-(bromomethyl)-4-(1H)-quinazolinone

To a suspension of 3,50 g of 6-methylquinazolone in 100 ml of chloroform is added 3.39 g of N-bromosuccinimide and 0.25 g of benzoyl peroxide. The reaction mixture is heated at reflux for 18 hours and then filtered hot. A precipitate of 2.21 g of an inseparable mixture of the desired bromide and starting 6-methyl-quinazolinone is obtained and used in Example 4 without further purification.

EXAMPLE 4

2-Butyl-6-(hydroxymethyl)-4(1H)-quinazolinone

To a suspension of 2.0 g of impure 2-butyl-6-(bromethyl)-4(1H)-quinazolinone (from Example 3) in 35 ml of dimethylsulfoxide and 20 ml of water is added 1.0 g of potassium carbonate. The reaction mixture is heated at reflux for 6 hours, resulting in a complete solution. Upon cooling slowly to room temperature a white precipitate forms and is collected by filtration. The filter cake is purified by flash chromatography on silica gel, eluting with 9:1 chloroform-methanol to give 0.67 g of the desired product as a white solid. CI MASS SPEC 233(MH+).

EXAMPLE 5

2-Butyl-1,4-dihydro-4-oxo-6-quinazolinecarboxaldehyde

To a solution of 0.3 g of 2-butyl-6-(hydroxymethyl)-4(1H)-quinazolinone in 3.5 ml of dry N,N-dimethylformamide is added 1.7 g of pyridinium dichromate. The reaction mixture is stirred at room temperature for 16 hours and then poured into 125 ml of water. The resulting precipitate is removed by filtration and the filtrate extracted with 9:1 chloroform-methanol. The combined organic extracts are dried over magnesium sulfate, filtered and concentrated in vacuo and combined with the precipitate above. The combined solids are purified by flash chromatography on silica gel by eluting with 1:1 ethyl acetate-hexanes to give 0.27 g of the desired product. CI MASS SPEC 231(MH+).

EXAMPLE 6

2-Butyl-6-(1-hydroxyethyl)-4(1H)-quinazolinone

To a solution of 0.60 g of 2-butyl-1,4-dihydro-4-oxo-6-quinazolinecarboxyaldehyde in 30 ml of dry tetrahydrofuran, cooled to 0° C. is added dropwise, 2.61 ml of a 3.0M solution of methylmagnesium bromide in diethyl ether. The reaction of stirred at 0° C. for 30 minutes and then quenched with 10 ml of aqueous ammonium chloride. After diluting with 10 ml of water, the reaction mixture is extracted with 9:1 chloroform-methanol. The combined extracts are dried with magnesium sulfate, filtered and concentrated to yield 0.64 g of the desired product. CI MASS SPEC 247(MH+).

EXAMPLE 7

2-Butyl-6-(1-hydroxypropyl)-4(1H)-quinazolinone

To a solution of 0.25 g of 2-butyl-1,4-dihydro-4-oxo-6-quinazolinecarboxaldehyde in 10 ml of dry tetrahydrofuran, cooled to 0° C., is added 1.63 ml of 2.0M ethyl magnesium bromide in tetrahydrofuran. The reaction mixture is stirred for 30 minutes at 0° C. and quenched with 20 ml of saturated ammonium chloride solution and 20 ml of water. The reaction mixture is extracted with 9:1 chloroform-methanol, dried over magnesium sulfate, filtered and evaporated in vacuo to give 0.26 g of the desired product. CI MASS SPEC 261(MH+).

EXAMPLE 8

2-Butyl-1,4-dihydro-4-oxo-6-quinazoline-carboxaldehyde

To a solution of 1.0 g of 2-butyl-6-iodo-4-(1H)-quinazolinone and 0.355 g of tetrakis(triphenylphosphine)palladium in 15 ml of tetrahydrofuran and 5 ml of N,N-dimethylformamide, heated to 55° C. under an atmosphere of carbon monoxide is added a solution of 1.40 g of tri-n-butyltin hydride in 2.5 ml of toluene over 6 hours via a syringe pump. After the addition is complete the reaction is allowed to cool to room temperature, diluted with brine and extracted with chloroform. The combined organics are concentrated in vacuo and the resulting residue triturated with ether. The precipitate is collected by filtration and purified by flash chromatography on silica gel, eluting with 1:1 ethyl acetate-hexanes to give 0.35 g of the desired product, m.p. 242°-244° C.

EXAMPLE 9

2-Butyl-6-[(trimethylsilyl)ethylnyl]-4(1H)quinazolinone

To a solution of 1.0 g of 2-butyl-6-iodo-4(1H)-quinazolinone 0.043 g of bis (triphenylphosphine) palladium (II) chloride and 5.8 mg of copper (I) iodide in 5.0 ml of N,N-dimethylformamide and 5.0 ml of triethylamine is added 0.36 g of (trimethylsilyl)acetylene. The resulting reaction mixture is heated at 45° C. for 1 hour and then 65° C. for 5 hours. Upon cooling, the reaction mixture is concentrated in vacuo and the residue purified by flash chromatography on silica gel, eluting with 1:3 ethyl acetate-hexane to yield 0.75 g of the desired product as a white solid. CI MASS SPEC 299(MH+).

EXAMPLE 10

2-Butyl-6-ethylnyl)-4-(1H)-quinazolinone

To a solution of 0.70 g of 2-butyl-6-[(trimethylsilyl)ethynyl]-4(1H)-quinazolinone in 20 ml of methanol and 20 ml of tetrahydrofuran is added 10.0 ml of 1.0 N sodium hydroxide solution. The reaction is stirred at room temperature for 2 hours and then diluted with 5% hydrochloric acid solution until the pH is 2. The resulting tan precipitate is collected by filtration and dried in vacuo to yield 0.50 g of the desired product. CI MASS SPEC 227(MH+).

EXAMPLE 11

6-Acetyl-2-butyl-4(1H)-quinazolinone

To a solution of 1.20 g of 2-butyl-6-ethynyl-4(1H)-quinazolinone in 90 ml of acetate acid is added 0.45 g of mercuric sulfate, 0.9 ml of water and 0.3 ml of sulfuric acid. The reaction mixture is heated at reflux for 5 hours, cooled to room temperature and quenched with 150 ml of water. The resulting mixture is concentrated in vacuo, diluted with 150 ml of water and extracted with 6:1 chloroform-methanol. The combined organics are dried over magnesium sulfate, filtered and concentrated in vacuo. The residue is purified by flash chromatography on silica gel, eluting with 1:1 ethyl acetate-hexanes to give 0.67 g of the desired product as a white solid. CI MASS SPEC 245(MH+).

EXAMPLE 12

2-Butyl-6-(1-hydroxy-1-methylethyl)-4(1H)-quinazolinone

To a solution of 4.00 g of 6-acetyl-2-butyl-4-(1H)-quinazolinone in 250 ml of dry tetrahydrofuran, cooled to 0° C., is added dropwise 16.4 ml of 3.0M methylmagnesium bromide in diethyl ether. The reaction is stirred at 0° C. for 0.5 hours and then allowed to warm to room temperature followed by quenching with 100 ml of saturated ammonium chloride solution. The mixture is diluted with 50 ml of water and extracted with ethyl acetate. The combined organic layers are washed with brine, dried over anhydrous magnesium sulfate, filtered and concentrated in vacuo. The residue is purified by flash chromatography on silica gel, eluting with 100:0.25 chloroform-methanol to give 2.75 g of the desired product as a white solid. CI MASS SPEC 261(MH+).

EXAMPLE 13

2-Butyl-6-(1-hydroxyethyl)-4(1H)-quinazolinone

To a suspension of 0.102 g of 6-acetyl-2-butyl-4(1H)-quinazolinone in 10.0 ml of ethanol is added 0.015 g of sodium borohydride. The reaction mixture is stirred for 1.5 hours at room temperature and then diluted with 50 ml of water. The aqueous layer is extracted with 5:1 chloroform-methanol and the combined organics dried over magnesuim sulfate, filtered and concentrated in vacuo to yield 0.103 g of the desired product. CI MASS SPEC 247(MH+).

EXAMPLE 14

Methyl 2-butyl-1,4-dihydro-4-oxo-6-quinazolinecarboxylate

To a solution of 1.00 g of 2-butyl-6-iodo-4(1H)-quinazolinone and 6.0 ml of triethylamine in 25 ml of methanol and 5 ml of N,N-dimethylformamide is added 0.275 g of bis-(triphenylphosphine)palladium (II) chloride. The reaction mixture is heated at reflux under an atmosphere of carbon monoxide for 16 hours, then allowed to cool and concentrated in vacuo. The residue is purified by flash chromatography on silica gel, eluting with 1:1 ethyl acetate-hexanes to give 0.389 g of the desired product as a white solid. CI MASS SPEC 261(MH+).

EXAMPLE 15

2-Butyl-6-(1-hydroxy-1-methylethyl)-4(1H)-quinazolinone

To a solution of 0.075 g of methyl 2-butyl-1,4-dihydro-4-oxo-6-quinazolinecarboxylate in 5 ml of dry tetrahydrofuran, cooled to 0° C., is added dropwise 0.51 mol of a solution of 3.0M methylmagnesium bromide in diethyl ether. The reaction is stirred at 0° C. for 0.5 hours and then at room temperature for 1 hour followed by quenching with 10 ml of saturated ammonium chloride solution. The resulting reaction mixture is diluted with 10 ml of water and extracted with ethyl acetate. The combined organics are dried over magnesium sulfate, filtered and concentrated in vacuo. The residue is purified by flash chromatography on silica gel, eluting with 100:0.25 chloroform-methanol to yield 0.055 g of the desired product as a white solid, m.p. 190°–192° C.

EXAMPLE 16

2-Butyl-6-(1-methylethenyl)-4(1H)-quinazolinone

To a suspension of 3.66 g of methyltriphenylphosphonium bromide in 30 ml of dry tetrahydrofuran, cooled to −78° C., is added dropwise 5.9 ml of a 1.73M solution of n-butyllithium in hexanes. Following complete addition, the reaction mixture is allowed to warm to room temperature and stirred for 15 minutes, until all the phosphonium bromide is dissolved. The reaction mixture is then recooled to −78° C. and a suspension of 6-acetyl-2-butyl-4(1H)-quinazolinone in 15 ml of dry tetrahydrofuran is added. The reaction is allowed to warm to room temperature and stirred for 24 hours followed by quenching with saturated ammonium chloride solution. After diluting with 10 ml of water, the aqueous layer is extracted with chloroform and the combined organics dried over magnesium sulfate, filtered and concentrated in vacuo. The residue is purified by flash chromatography on silica gel, eluting with 1:2 ethyl acetate-hexanes to give 0.23 g of the desired product as a white solid. CI MASS SPEC 243(MH+).

EXAMPLE 17

2-Butyl-6-(hydroxyphenylmethyl)-4(1H)-quinazolinone

To a stirred solution of 2.00 g of 2-butyl-1,2-dihydro-4-oxo-6-quinazolinecarboxaldehyde in 100 ml of tetrahydrofuran, cooled at 0° C., is added 13.0 ml of 2.0 M phenyllithium and stirring continued for 1 hour. The cooling is removed and the reaction allowed to reach room temperature followed by an additional 30 minutes at room temperature. The reaction is diluted with saturated ammonium chloride solution and extracted with ethyl acetate. The organic layer is dried, evaporated to a residue, which is purified by chromatography on silica gel by elution with 0.25:100 methanol-chloroform to give 0.932 g of the desired product. CI MASS SPEC 309(MH+).

EXAMPLE 18

2-Butyl-6-ethenyl-4(H)-quinazolinone

A mixture of 2.00 g of 2-butyl-6-ethylnyl-4(1H)-quinazolinone and 0.200 g 5% palladium-barium sulfate in 100 ml of pyridine is treated with 1 atmosphere of hydrogen at room temperature until 225 ml of hydrogen is used. The reaction mixture is filtered through diatomaceous earth and the cake washed with 100 ml of pyridine and 100 ml of methanol. The combined filtrates are evaporated to a residue which is purified by chromatography on silica gel using 1:2 ethyl acetate-hexanes to afford 0.786 g of the desired product. CI MASS SPEC 229(MH+).

EXAMPLE 19

2-Butyl-6-ethenyl-4(1H)-quinazolinone

A mixture of 12.28 g of 2-butyl-6-iodo-4(1H)-quinazolinone 0.866 g of tetrakis (triphenylphosphine)-palladium, 0.015 g of 2,6-di-t-butyl-4-methylphenol in 75 ml of toluene and 20 ml of N,N-dimethylformamide is treated with 13.06 g of vinyltin followed by heating at reflux for 4 hours. The reaction mixture is cooled and concentrated in vacuo. The residue is diluted with hexanes and filtered. The filter cake is washed with hexanes and the remaining tacky solid dissolved in 100 ml of chloroform-methanol (8:2) and purified by chromatography on silica gel with 1:3 ethyl acetate-hexanes to afford 4.55 g of the desired product as a yellow solid. CI MASS SPEC 229(MH+).

EXAMPLE 20

2-Butyl-6-(1-hydroxyethyl)-3-[[2′-[1-triphenyl-methyl)-1H-tetrazol-5-yl][1,1′-biphenyl]-4-yl]-methyl]-4(3H)-quinazolinone A suspension of 2.50 g of 2-butyl-6-(1-hydroxyethyl)-4(1H)-quinazolinone, 6.79 g of 5-[4′-(bromomethyl)[1,1′-biphenyl]-2-yl]-1-(triphenylmethyl)-1H-tetrazole and 4.20 g of anhydrous potassium carbonate in 225 ml of dry acetone is heated at reflux for 16 hours. The reaction mixture is allowed to cool to room temperature, filtered and the filtrate evaporated in vacuo. The residue is purified by high pressure liquid chromatography on silica gel by eluting with 1:2 ethyl acetate-hexanes to afford 4.25 g of the desired product as a white solid, FAB M+H 723.

Examples 21–27 in Table II are prepared under substantially the same alkylation conditions as Example 20 from the appropriately substituted quinazolinone starting materials.

TABLE I

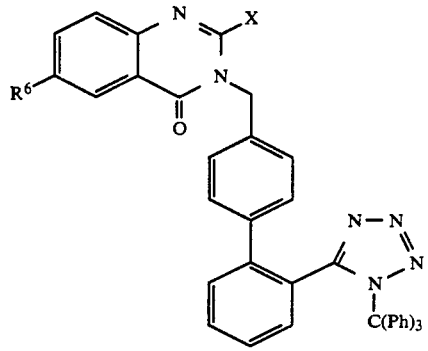

| Ex. No. | R⁶ | X | FAB Low Resolution Mass Spectrum |
|---|---|---|---|
| 21 | —C≡C—H | —(CH₂)₃CH₃ | 703 (M+H) |
| 22 | —CH₂OH | —(CH₂)₃CH₃ | 709 (M+H) |
| 23 | —CH(OH)CH₂CH₃ | —(CH₂)₃CH₃ | 737 (M+H) |
| 24 | —CO₂CH₃ | —(CH₂)₃CH₃ | 737 (M+H) |
| 25 | —C(O)—CH₃ | —(CH₂)₃CH₃ | 721 (M+H) |
| 26 | CH=CH₂ | —(CH₂)₃CH₃ | 705 (M+H) |
| 27 | —CH(OH)C₆H₅ | —(CH₂)₃CH₃ | 807 (M+Na) |

EXAMPLE 28

2-Butyl-6-[[(methylsulfonyl)oxy]methyl]-3-[[2′-[1-(triphenylmethyl)-1H-tetrazol-5-yl][1,1′-biphenyl]-4-yl]methyl]-4(3H)-quinazolinone A stirred solution of 0.250 g of 2-butyl-6-(hydroxymethyl)-3-[[2′-[1-(triphenylmethyl)-1H-tetrazol-5-yl][1,1′-biphenyl]-4-yl]methyl]-4(3H)-quinazolinone and 0.246 ml of triethylamine in 5.0 ml of tetrahydrofuran is cooled to −78° C. and 0.137 ml of methanesulfonyl chloride added. The reaction mixture is allowed to warm to room temperature and continue stirring for 18 hours. The reaction mixture is partitioned between chloroform and water. The organic layer is washed with aqueous 5% HCl, water and saturated aqueous sodium bicarbonate then dried with magnesium suflate and evaporated to afford 0.278 g of the desired product. FAB MASS SPEC 787 (M+H).

EXAMPLE 29

2-Butyl-6-(phenoxymethyl)-3-[[2'-[1-(triphenylmethyl)-1H-tetrazol-5-yl][1,1'-biphenyl]-4-yl]methyl]-4(3H)-quinazolinone A mixture of 0.278 of 2-butyl-6-[[(methylsulfonyl)oxy]methyl]-3-[[2'-[1-(triphenylmethyl)-1H-tetrazol-5-yl[]1,1'-biphenyl]-4-yl]methyl]-4(3H)-quinazolinone. (Example 28), 0.067 g of phenol and 0.098 g of potassium carbonate in 5.0 ml of acetone is refluxed for 18 hours. The volatiles are evaporated in vacuo after filtering. The concentrate is purified by chromatography on silica gel using 1:4 ethyl acetate-hexanes to afford 0.196 g of the desired product. FAB MASS SPEC 807 (M+Na).

Examples 30–35 in Table II are prepared under substantially the same conditions as Example 2 from the appropriately substituted phenol starting material.

TABLE II

| Ex. No. | $R^6$ | X |
|---|---|---|
| 30 | 2-F-phenyl-O—$CH_2$— | —$(CH_2)_3CH_3$ |
| 31 | 3-$CH_3$O-phenyl-O—$CH_2$— | —$(CH_2)_3CH_3$ |
| 32 | 3-$CF_3$-phenyl-O—$CH_2$— | —$(CH_2)_3CH_3$ |
| 33 | 3-$CH_3$-phenyl-O—$CH_2$— | —$(CH_2)_3CH_3$ |
| 34 | 4-$NO_2$-phenyl-O—$CH_2$— | —$(CH_2)_3CH_3$ |
| 35 | 4-Cl-phenyl-O—$CH_2$— | —$(CH_2)_3CH_3$ |

EXAMPLE 36

2-Butyl-6-(phenoxymethyl)-3-[[2'-(1H-tetrazol-5-yl)[1,1'-biphenyl]-4-yl]methyl]-4(3H)-quinazolinone A mixture of 0.186 g of 2-butyl-6-(phenoxymethyl)-3-[[2'-[1-(triphenylmethyl)-1H-tetrazol-5-yl]-[1,1'-biphenyl]-4-yl]methyl-4(3H)-quinazolinone (Example 29) in 3.0 ml of 3.0 M HCl in ethyl acetate and 5.0 ml of ether is stirred at room temperature for one hour. The reaction mixture is diluted with 10 ml of ether and filtered. The cake is washed with ether and hexanes then dried to afford 0.117 g of the desired compound as a solid. FAB MASS SPEC 543(M+H).

Examples 37–42 in Table III are prepared from the triphenylmethyl protected compounds of Examples 29–35 under substantially the same conditions as Example 36.

TABLE III

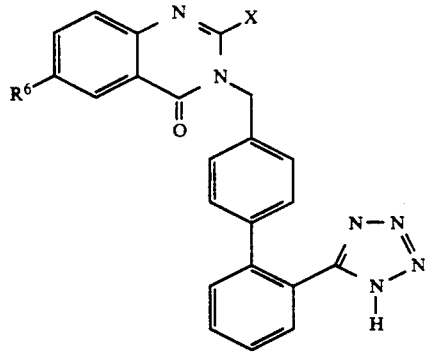

| Ex. No. | $R^6$ | X |
|---|---|---|
| 37 | 2-F-phenyl-O—$CH_2$— | —$(CH_2)_3CH_3$ |
| 38 | 3-$CH_3$O-phenyl-O—$CH_2$— | —$(CH_2)_3CH_3$ |
| 39 | 3-$CF_3$-phenyl-O—$CH_2$— | —$(CH_2)_3CH_3$ |
| 40 | 3-$CH_3$-phenyl-O—$CH_2$— | —$(CH_2)_3CH_3$ |
| 41 | 4-$NO_2$-phenyl-O—$CH_2$— | —$(CH_2)_3CH_3$ |
| 42 | 4-Cl-phenyl-O—$CH_2$— | —$(CH_2)_3CH_3$ |

Angiotensin II Antagonists In Vitro Tests Materials and Methods

Beef adrenals are obtained from a local slaughter house (Maxwell-Cohen). [$^{125}$I](Sar$^1$,-Ile$^8$)AngII, S.A. 2200 Ci/mmole, is purchased from Dupont (NEN®, Boston, Mass.). All unlabeled AngII analogs, dimethylsulfoxide (DMSO), nucleotides, bovine serum albumin (BSA) are purchased from Sigma Chemical Co., St. Louis, Mo. U.S.A.

Preparation of Membranes

Approximately sixteen (16) to twenty (20) beef adrenal glands are processed as follows: fresh adrenal glands received on crushed ice are cleaned of fatty tissues and the tough membranes encapsulating the glands are removed and discarded. The brownish tissue forming the adrenal cortex is scraped off and finely minced with scissors before homogenization. Care is taken to avoid contamination with medullary tissue during dissection. The scraped cortices are suspended in twenty volumes of an ice-cold buffer medium consisting of 10 mM Tris.HCl (pH 7.4 at 22° C.) and containing 1.0 mM EDTA and 0.2M sucrose. Unless otherwise indicated, all subsequent operation are done at 4° C. The tissue is homogenized in a glass homogenizer with a motor-driven teflon pestle with a clearance of 1.0 mm. The homogenate is centrifuged first at low speed (3,000×g) for 10 min. The resulting pellet is discarded and the supernatant fluid recentrifuged at 10,000×g for 15 minutes to give a P$_2$ pellet. This P$_2$ pellet is discarded and the liquid phase is carefully decanted off in clean centrifuge tubes and recentrifuged at high speed (100,000×g) for 60 min. The translucent final pellet is harvested and combined in a small volume (20–50.0 ml) of 50.0 mM Tris.HCl buffer, pH 7.2. A 100 ul aliquot is withdrawn and the protein content of the preparation is determined by the Lowry's method (Lowry, O. H., Rosebrough, N. F., Farr, A. L. and Randall, R. J., Protein measurement with Folin phenol reagent. J. Biol. Chem., 48, 265–275, 1951). The pelled membrane is reconstituted in 50.0 mM Tris.HCl buffer containing 0.1 mM of phenylmethylsulfonyl fluoride (PMSF) to give approximately a protein concentration of 2.5 mg per ml of tissue suspension. The membrane preparation is finally aliquoted in 1.0 ml volumes and stored at −70° C. until use in the binding assays.

Receptor Binding Assay

Binding of [$^{125}$I](Sar$^1$,Ile$^8$)AngII

The binding of [$^{125}$I](Sar$^1$,Ile$^8$)AngII to microsomal membranes is initiated by the addition of reconstituted membranes (1:10 vols.) in freshly made 50.0 mM Tris.HCl buffer, pH 7.4 containing 0.25% heat inactivated bovine serum albumin (BSA): 80 ul membrane protein (10 to 20 ug/assay) to wells already containing 100 ul of incubation buffer (as described above) and 20 ul [$^{125}$I[(Sar$^1$,Ile$^8$)AngII (Specific Activity, 2200 Ci/m-mole). Non-specific binding is measured in the presence of 1.0 uM unlabeled (Sar$^1$,Ile$^8$)AngII, added in 20 ul volume. Specific binding for [$^{125}$I](Sar$^1$,Ile$^8$) AngII is greater than 90%. In competition studies, experimental compounds are diluted in dimethylsulfoxide (DMSO) and added in 20 ul is wells before the introduction of tissue membranes. This concentration of DMSO is found to have no negative effects on the binding of [$^{125}$I] (Sar$^1$,Ile$^8$) AngII to the membranes. Assays are performed in triplicate. The wells are left undisturbed for 60 min. at room temperature. Following incubation, all wells are harvested at once with a Brandel ® Harvester especially designed for a 96 well plate (Brandel ® Biomedical Research & Development Labs. Inc., Gaithersburg, Md. U.S.A.). The filter discs are washed with 10×1.0 ml of cold 0.9% NaCl to remove unbound ligand. Presoaking the filter sheet in 0.1% polyethyleneimine in normal saline (PEI/Saline) greatly reduces the radioactivity retained by the filter blanks. This method is routinely used. The filters are removed from the filter grid and counted in a Parkard ® Cobra Gamma Counder for 1 min. (Packard Instrument Co., Downers Grove, Ill., U.S.A.). The binding data are analyzed by the non-linear interactive "LUNDON-1" program (LUNDON SOFTWARE Inc., Cleveland, Ohio U.S.A.). Compounds that displace 50% of the labelled angiotensin II at the screening dose of 50 μM are considered active compounds and are then evaluated in concentration-response experiments to determine their IC$_{50}$ values. The results are shown in Table IV.

TABLE IV

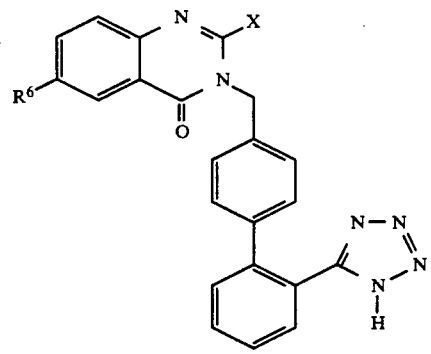

| Ex. No. | R$^6$ | X | Angiotensin II Receptor Binding IC$_{50}$ (M) |
|---|---|---|---|
| 36 | phenyl-O—CH$_2$— | —(CH$_2$)$_3$CH$_3$ | 13 × 10$^{-8}$ |

As can be seen from the above table, the compound demonstrates excellent activity.

The enzyme renin acts on a blood plasma α$_2$-globulin, angiotensinogen, to produce angiotensin I, which is then converted by angiotensin converting enzyme to AII. The substance AII is a powerful vasopressor agent which is implicated as a causative agent for producing high blood pressure in mammals. Therefore, compounds which inhibit the action of the hormone angiotensin II (AII) are useful in alleviating angiotensin induced hypertension.

When the compounds are employed for the above utility, they may be combined with one or more pharmaceutically acceptable carriers, for example, solvents, diluents and the like, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspension containing from about 0.05 to 5% suspending agent in an isotonic medium. Such pharmaceutical preparations may contain, for example, from about 0.05 up to about 90% of the active ingredient in combination with the carrier, more usually between about 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 0.5 to about 500 mg/kg of animal body weight, preferably given in divided doses two to four times a day, or in sustained release form. For most large mammals the total daily dosage is from about 1 to 100 mg, preferably from about 2 to 80 mg. Dosage forms suitable for internal use comprise from about 0.5 to 500 mg of the active compound in intimate admixture with a solid or liquid pharmaceutically acceptable carrier. This dosage regimen may be adjusted to provide the optical therapeutic response. For example, several divided doses may be administered daily or the dose may be proportionally reduced as indicated by the exigencies of the therapeutic situation.

These active compounds may be administered orally as well as by intravenous, intramuscular, or subcutaneous routes. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsulses. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

What is claimed is:

1. A quinazolinone compound having the formula:

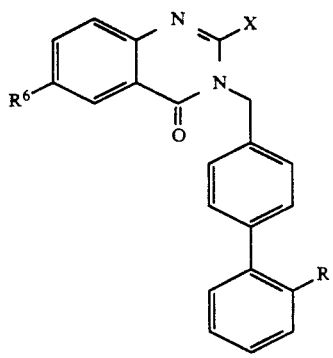

wherein:
R is

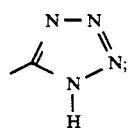

X is straight or branched chain lower alkyl of 3 to 5 carbon atoms;
n is 0 to 3;
$R^6$ is

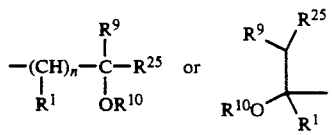

where $R^1$, $R^9$ and $R^{25}$, can be the same or different; $R^1$ is H, straight or branched chain lower alkyl of 1 to 4 carbon atoms, phenyl, substituted phenyl (substitution selected from mono-lower alkyl of 1 to 4 carbon atoms, —$CF_3$, —$NH_2$, nitro, O-alkyl of 1 to 4 carbon atoms, F, Cl., Br), pyridinyl, thienyl, or furyl; $R^9$ is H, straight or branched chain lower alkyl of 1 to 4 carbon atoms, phenyl, substituted phenyl (substitution selected from mono-lower alkyl of 1 to 4 carbon atoms, —$CF_3$, —$NH_2$, nitro, O-alkyl of 1 to 4 carbon atoms, F, Cl, Br) pyridinyl, thienyl, or furyl;

$R^{10}$ is phenyl, substituted phenyl (substitution selected from mono-lower alkyl of 1 to 4 carbon atoms, —$CF_3$, —$NH_2$, F, Cl, Br, nitro, or O-alkyl of 1 to 4 carbon atoms);

$R^{25}$ is H, straight or branched chain lower alkyl of 1 to 4 carbon atoms, phenyl, substituted phenyl (substitution selected from mono-lower alkyl of 1 to 4 carbon atoms, —$CF_3$, —$NH_2$, nitro, O-alkyl of 1 to 4 carbon atoms, F, Cl, Br), pyridinyl, thienyl, or furyl; or pharmaceutically acceptable salts thereof.

2. The compound according to claim 1 wherein said salts are selected from potassium, sodium calcium, magnesium or ammonium.

3. The compound according to claim 1 wherein X is a straight chain alkyl of 3 or 4 carbon atoms; $R_6$ is

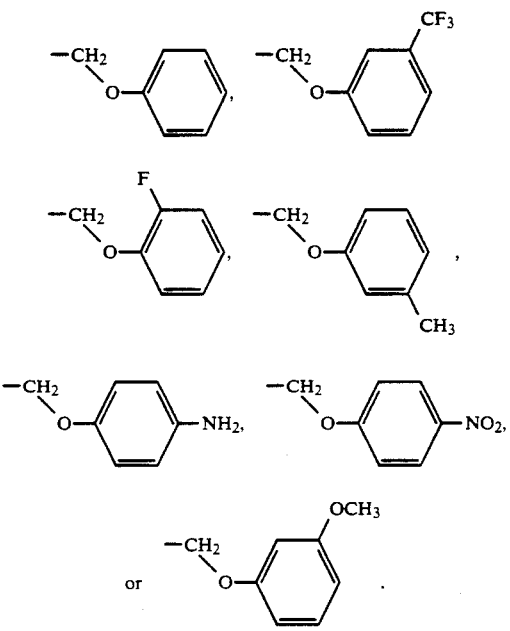

4. A quinazolinone compound having the formula:

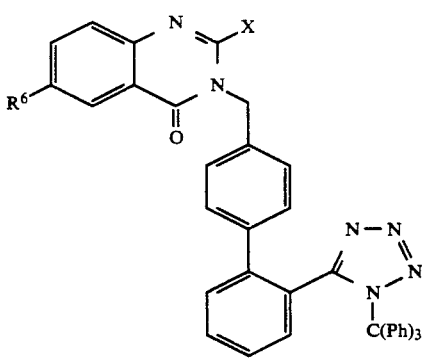

wherein:
X is straight or branched chain lower alkyl of 3 to 5 carbon atoms;
n is 0 to 3;
$R^6$ is

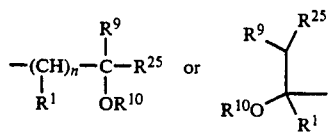

where $R^1$, $R^9$ and $R^{25}$ are the same or different;

$R^1$ is H, straight or branched chain lower alkyl of 1 to 4 carbon atoms, phenyl, substituted phenyl (substitution selected from mono-lower alkyl of 1 to 4 carbon atoms, —$CF_3$, —$NH_2$, nitro, O-alkyl of 1 to 4 carbon atoms, F, Cl, Br), pyridinyl, thienyl or furyl;

$R^9$ is H, straight or branched chain lower alkyl of 1 to 4 carbon atoms, phenyl, substituted phenyl (substitution selected from mono-lower alkyl of 1 to 4 carbon atoms, —$CF_3$, —$NH_2$, nitro, O-alkyl of 1 to 4 carbon atoms, F, Cl, Br), pyridinyl, thienyl or furyl;

$R^{10}$ is phenyl, substituted phenyl (substitution selected from mono-lower alkyl of 1 to 4 carbon atoms, —$CF_3$, —$NH_2$, F, Cl, Br, nitro, or O-alkyl of 1 to 4 carbon atoms);

$R^{25}$ is H, straight or branched chain lower alkyl of 1 to 4 carbon atoms, phenyl, substituted phenyl (substitution selected from mono-lower alkyl of 1 to 4 carbon atoms, —$CF_3$, —$NH_2$, nitro, O-alkyl of 1 to 4 carbon atoms, F, Cl, Br), pyridinyl, thienyl or furyl;

5. The compound according to claim 4 wherein X is a straight chain alkyl of 3 or 4 carbon atoms; $R_6$ is

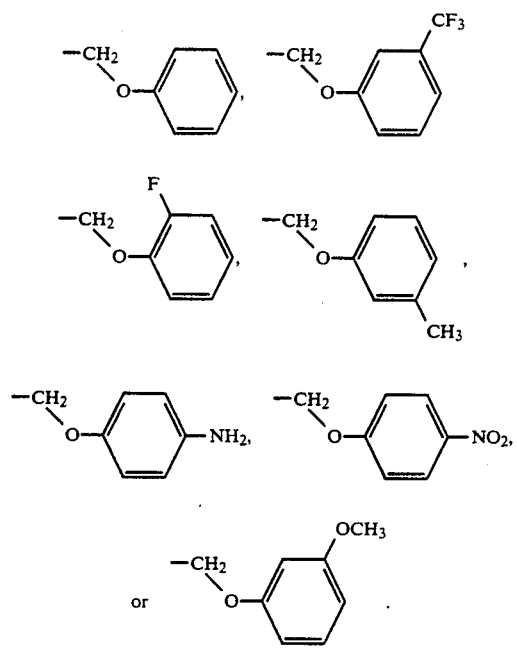

6. A quinazolinone compound having the formula:

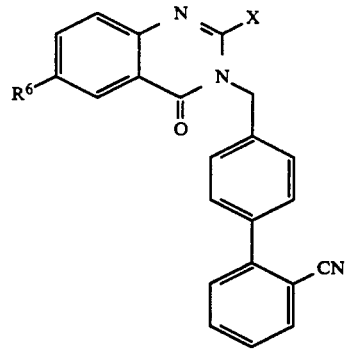

wherein:
X is straight or branched chain lower alkyl of 3 to 5 carbon atoms;
n is 0 to 3;
$R^6$ is

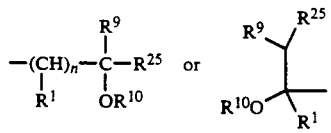

where $R^1$, $R^9$ and $R^{25}$ can be the same or different;

$R^1$ is H, straight or branched chain lower alkyl of 1 to 4 carbon atoms, phenyl, substituted phenyl (substitution selected from mono-lower alkyl of 1 to 4 carbon atoms, —$CF_3$, —$NH_2$, nitro, O-alkyl of 1 to 4 carbon atoms, F, Cl., Br), pyridinyl, thienyl or furyl;

$R^9$ is H, straight or branched chain lower alkyl of 1 to 4 carbon atoms, phenyl, substituted phenyl (substitution selected from mono-lower alkyl of 1 to 4 carbon atoms, —$CF_3$, —$NH_2$, nitro, O-alkyl of 1 to 4 carbon atoms, F, Cl, Br), pyridinyl, thienyl or furyl;

$R^{10}$ is phenyl, substituted phenyl (substitution selected from mono-lower alkyl of 1 to 4 carbon atoms, —$CF_3$, —$NH_2$, F, Cl, Br, nitro, or O-alkyl of 1 to 4 carbon atoms);

$R^{25}$ is straight or branched chain lower alkyl of 1 to 4 carbon atoms, phenyl, substituted phenyl (substitution selected from mono-lower alkyl of 1 to 4 carbon atoms, —$CF_3$, —$NH_2$, nitro, O-alkyl of 1 to 4 carbon atoms, F, Cl, Br), pyridinyl, thienyl or furyl;

7. The compound according to claim 6 wherein X is a straight chain alkyl of 3 or 4 carbon atoms; $R_6$ is

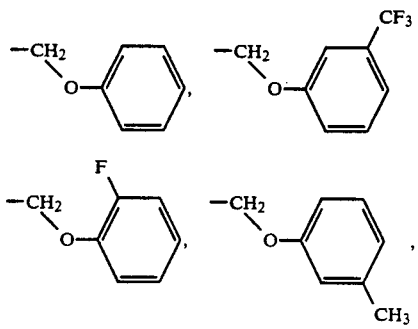

-continued

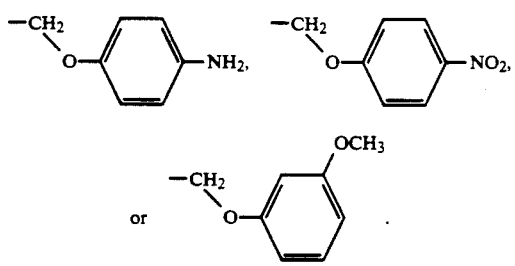

8. The compound according to claim 1, 2-butyl-6-(phenoxymethyl)-3-[[2'-(1H-tetrazol-5-yl)-[1,1'-biphenyl]-4-yl]methyl]-4(3H)-quinazolinone.

9. The compound according to claim 1, 2-butyl-6-[(2-fluorophenoxy)methyl]-3-[[2'-(1H-tetrazol-5yl)[1,1'-biphenyl]-4-yl]methyl]-4(3H)-quinazolinone.

10. The compound according to claim 1, 2-butyl-6-[[3-(trifluoromethyl)phenoxy]methyl]-3-[[2'-(1H)tetrazol-5-yl)[1,1'-biphenyl]-4-yl]methyl]-4(3H)-quinazolinone.

11. The compound according to claim 1, 2-butyl-6-[(3-methylphenoxy)methyl]-3-[[2'-(1H-tetrazol-5-yl)[1,1'-biphenyl]-4-yl]methyl]-4(3H)-quinazolinone.

12. The compound according to claim 1, 2-butyl-6-[(4-nitrophenoxy)methyl]-3-[[2'-(1H-tetrazol-5-yl)[1,1'-biphenyl]-4-yl]-4(3H)-quinazolinone.

13. The compound according to claim 1, 2-butyl-6-[(3-methoxyphenoxy)methyl]-3-[[2'-(1H-tetrazol-5-yl)[1,1'-biphenyl]-4-yl]methyl]-4(3H)-quinazolinone.

14. The compound according to claim 1, 2-butyl-6-[(4-chlorophenoxy)methyl]-3-[[2'-(1H-tetra-zol 5-yl)[1,1'-biphenyl]-4-yl]methyl]-4(3H)-quinazolinone.

15. The compound according to claim 4, 2-butyl-6-(phenoxymethyl)-3-[[2'-[1-(triphenylmethyl)-1H-tetrazol-5-yl][1,1'-biphenyl]-4-yl]methyl]-4(3H)-quinazolinone.

16. The compound according to claim 4, 2-butyl-6-[(2-fluorophenoxy)methyl]-3-[[2'-[1-(triphenylmethyl)-1H-tetrazol-5-yl][1,1'-biphenyl]-4-yl]-methyl]-4(3H)-quinazolinone.

17. The compound according to claim 4, 2-butyl-6-[[3-(trifluoromethyl)phenoxy]methyl]-3-[[2'-[1-(triphenylmethyl)-1H-tetrazol-5-yl][1,1'-biphenyl]-4-yl]methyl]-4(3H)-quinazolinone.

18. The compound according to claim 4, 2-butyl-6-[(3-methylphenoxy)methyl]-3-[[2'-[1-(triphenylmethyl)-1H-tetrazol-5-yl][1,1'-biphenyl]-4-yl]-methyl]-4(3H)-quinazolinone.

19. The compound according to claim 4, 2-butyl-6-[(4-nitrophenoxy)methyl]-3-[[2'-[1-(triphenylmethyl)-1H-tetrazol-5-yl][1,1'-biphenyl]-4-yl-methyl]-4(3H)-quinazolinone.

20. The compound according to claim 4, 2-butyl-6-[(3-methoxyphenoxy)methyl]-3-[[2'-[1-(triphenylmethyl)-1H-tetrazol-5-yl][1,1'-biphenyl]-4-yl]-methyl]-4(3H)-quinazolinone.

21. The compound according to claim 4, 2-butyl-6-[(4-chlorophenoxy)methyl]-3-[[2'-[1-(triphenylmethyl)-1H-tetrazol-5-yl][1,1'-biphenyl]-4-yl]methyl]-4(3H)-quinazolinone.

22. A pharmaceutical composition useful for treating angiotensin induced hypertension or congestive heart failure in a mammal comprising a suitable pharmaceutical carrier and an effective amount of a compound of claim 1.

23. A method of treating angiotensin induced hypertension in a mammal comprising administering a compound of claim 1 to said mammal in an amount effective to lower angiotensin induced hypertension.

24. A method of treating congestive heart failure in a mammal comprising administering a compound of claim 1 to said mammal in an amount effective to treat congestive heart failure.

25. A method of antagonizing the effects of Angiotensin II in a mammal comprising administering a compound of claim 1 to said mammal in an amount effective to treat the effects of Angiontensin II.

* * * * *